US010823616B2

(12) United States Patent
Smith et al.

(10) Patent No.: US 10,823,616 B2
(45) Date of Patent: Nov. 3, 2020

(54) DUAL SENSOR AND METHOD FOR DETECTION OF AN ANALYTE GAS

(71) Applicant: The Boeing Company, Chicago, IL (US)

(72) Inventors: Robert A. Smith, Hampton Cove, AL (US); David K. Mefford, Huntsville, AL (US)

(73) Assignee: The Boeing Company, Chicago, IL (US)

( * ) Notice: Subject to any disclaimer, the term of this patent is extended or adjusted under 35 U.S.C. 154(b) by 40 days.

(21) Appl. No.: 16/290,219

(22) Filed: Mar. 1, 2019

(65) Prior Publication Data

US 2019/0368935 A1     Dec. 5, 2019

Related U.S. Application Data

(60) Provisional application No. 62/678,370, filed on May 31, 2018.

(51) Int. Cl.
    *G01J 3/433*      (2006.01)
    *G01N 33/53*      (2006.01)
    *G01N 21/39*      (2006.01)

(52) U.S. Cl.
    CPC .......... *G01J 3/4338* (2013.01); *G01N 21/39* (2013.01); *G01N 33/5306* (2013.01)

(58) Field of Classification Search
    CPC .... G01J 3/28; G01J 3/4338; G01J 3/42; G01J 3/0237; G01J 3/108; G01J 3/26; G01J 3/457; G01J 3/36; G01J 3/0248; G01J 2003/2866; G01J 2003/104; G01J 2003/102; G01J 2003/423; G01N 21/3504; G01N 21/3581; G01N 21/39; G01N 2021/3513; G01N 33/5306
    See application file for complete search history.

(56) References Cited

U.S. PATENT DOCUMENTS

| | | | | |
|---|---|---|---|---|
| 5,434,412 | A | * 7/1995 | Sodickson | A61B 5/14532 250/343 |
| 2006/0128034 | A1 | * 6/2006 | Petruno | G01N 21/6428 436/524 |

(Continued)

OTHER PUBLICATIONS

Elsevier; Biosensors & Bioelectronics 21 (2006), "*Plastic Antibody for the Recognition of Chemical Warfare Agent Sulphur Mustard*", Jan. 11, 2006, (pp. 2339-2344).

(Continued)

*Primary Examiner* — Sang H Nguyen
(74) *Attorney, Agent, or Firm* — Walters & Wasylyna LLC

(57) ABSTRACT

A dual sensor, includes: one or more analyte detectors, each having an analyte-specific binding site for interacting with a specific analyte; an optical source generating a first frequency comb spectrum directed to an environment to be scanned, the first frequency comb spectrum having multiple optical frequencies at a first frequency range; an optical spectrum analyzer analyzing an optical spectrum resulting from interaction of the first frequency comb spectrum with the environment; and a controller that is configured, where an analyte detector indicates presence of a specific analyte, to adjust the first frequency comb spectrum to increase sensitivity for detecting the specific analyte.

20 Claims, 6 Drawing Sheets

(56) References Cited

U.S. PATENT DOCUMENTS

| | | | |
|---|---|---|---|
| 2009/0002701 A1* | 1/2009 | Fattal | B82Y 15/00 356/301 |
| 2009/0209883 A1* | 8/2009 | Higgins | A61B 5/15174 600/575 |
| 2011/0043815 A1* | 2/2011 | Giaccari | G01J 3/45 356/451 |
| 2011/0058248 A1* | 3/2011 | Vodopyanov | G02F 1/39 359/330 |
| 2012/0002212 A1 | 1/2012 | Chandler et al. | |
| 2012/0183949 A1 | 7/2012 | Hyde et al. | |
| 2012/0263922 A1 | 10/2012 | Advincola et al. | |
| 2013/0337477 A1* | 12/2013 | Kuhr | G01N 1/4022 435/7.92 |
| 2015/0159990 A1* | 6/2015 | Plusquellic | G01J 3/453 356/451 |
| 2016/0282264 A1* | 9/2016 | Wagner | G01N 21/3577 |
| 2017/0059403 A1* | 3/2017 | Froehlich | G01J 3/0208 |
| 2017/0201328 A1 | 7/2017 | Hugi et al. | |
| 2017/0256909 A1* | 9/2017 | Braddell | G01J 3/42 |
| 2018/0309941 A1* | 10/2018 | Lopez | G01J 3/45 |
| 2019/0167112 A1* | 6/2019 | Kane | A61B 5/14546 |

OTHER PUBLICATIONS

RSC Publishing, "*High-Performance $H^2S$ Detection by Redox Reactions in Semiconductung Carbon Nanotube-Based Devices*", Sep. 26, 2013, (pp. 7206-7211).

CLEO 2018, "*Dual-Cavity Scanning Comb Spectroscopy*", (pp. 1-2).

\* cited by examiner

DUAL SENSOR AND METHOD FOR DETECTION OF AN ANALYTE GAS

PRIORITY

This application claims priority from U.S. Ser. No. 62/678,370 filed on May 31, 2018.

FIELD

The present application relates to the field of chemical species detection.

BACKGROUND

Conventional laser spectroscopy systems interrogate a chemical one wavelength at a time. In many cases, a limitation of current optical systems is their inability to have specific detection of some chemicals due to interference from other spectra or their inability to see a signal of interest due to a high background signature of other chemicals being present. Corroborating systems use laboratory approaches like mass spectrometry or chemical analysis which take considerable time that can range from hours to days.

Accordingly, those skilled in the art continue with research and development in the field of chemical species detection.

SUMMARY

In one embodiment, a dual sensor, includes: one or more analyte detectors, each having an analyte-specific binding site for interacting with a specific analyte; an optical source generating a first frequency comb spectrum directed to an environment to be scanned, the first frequency comb spectrum having multiple optical frequencies at a first frequency range; an optical spectrum analyzer analyzing an optical spectrum resulting from interaction of the first frequency comb spectrum with the environment; and a controller that is configured, where an analyte detector indicates presence of a specific analyte, to adjust the first frequency comb spectrum to increase sensitivity for detecting the specific analyte.

In another embodiment, a dual sensor, includes: a plurality of analyte detectors, each having an analyte-specific binding site for interacting with a different specific analyte; an optical source generating a first frequency comb spectrum and a second frequency comb spectrum directed to the environment to be scanned, the first frequency comb spectrum having multiple optical frequencies at a first frequency range and the second frequency comb spectrum having multiple optical frequencies at a second frequency range different from the first frequency range; an optical spectrum analyzer analyzing an optical spectrum resulting from interaction of the first and second frequency comb spectrums with the environment; and a controller that is configured, where an analyte detector indicates presence of a specific analyte, to adjust the first and second frequency comb spectrums to increase sensitivity for detecting the specific analyte.

In yet another embodiment, a method for detection of an analyte gas includes: exposing one or more analyte detectors to an environment, each analyte detector having an analyte-specific binding site for interacting with a specific analyte; identifying presence of a specific analyte based on an analyte detector; optically scanning the environment with a first frequency comb spectrum, wherein the first frequency comb spectrum is adjusted to a predetermined spectral range corresponding to the identified specific analyte to increase sensitivity for detecting the identified specific analyte; and analyzing an optical spectrum resulting from interaction of the first frequency comb spectrum with the environment.

Other embodiments of the disclosed dual sensor and method for detection of an analyte gas will become apparent from the following detailed description, the accompanying drawings and the appended claims.

DETAILED DESCRIPTION

Figure 1:
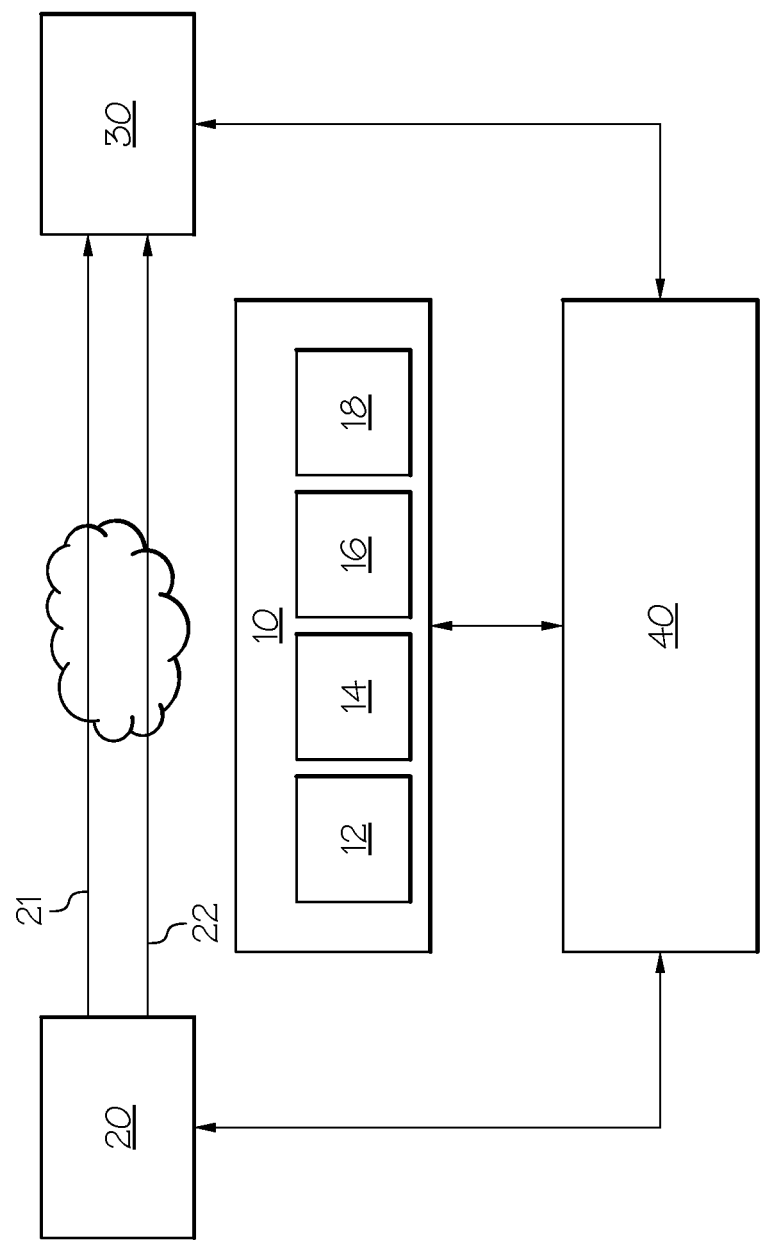
FIG. 1 is a schematic diagram representing a dual sensor according to the present description.
Figure 2:
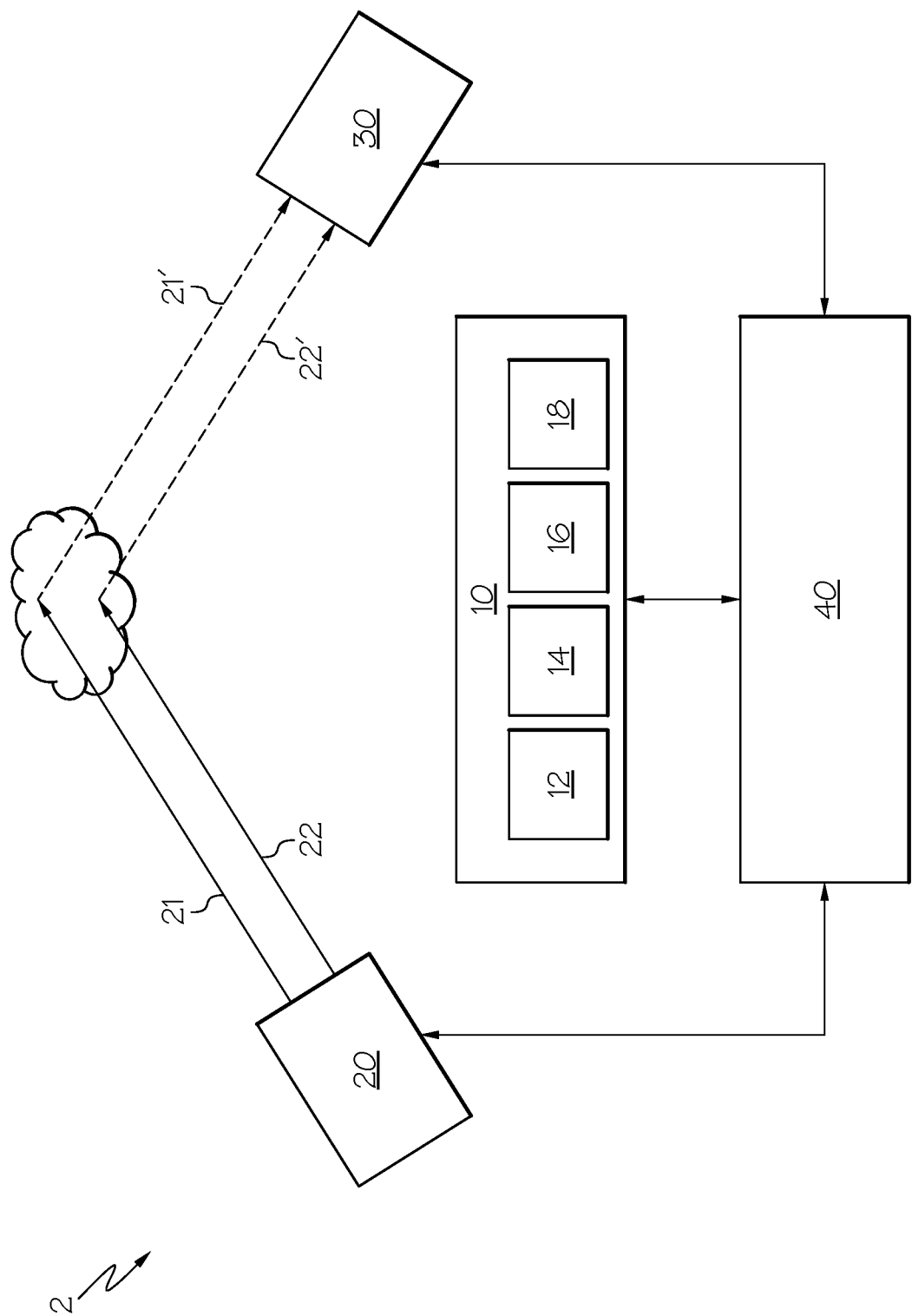
FIG. 2 is a schematic diagram representing a variation of the dual sensor of FIG. 1.

FIG. 1 is a schematic diagram representing a dual sensor 2 according to the present description. FIG. 2 is a schematic diagram representing a variation of the dual sensor 2 of FIG. 1. As shown in FIGS. 1 and 2, the dual sensor 2 includes one or more analyte detectors 10, an optical source 20, an optical spectrum analyzer 30, and a controller 40.

In the illustrated example, the one or more analyte detectors 10 include a plurality of analyte detectors, such as a first analyte detector 12, a second analyte detector 14, a third analyte detector 16, and a fourth analyte detector, each of the analyte detectors having an analyte-specific binding site for interacting with a specific analyte. In an aspect, each of the analyte detectors has an analyte-specific binding site for interacting with a different specific analyte, such that the analyte detector 12 has an analyte-specific binding site for interacting with a first specific analyte, the analyte detector 14 has an analyte-specific binding site for interacting with a second specific analyte, the analyte detector 16 has an analyte-specific binding site for interacting with a third specific analyte, and the analyte detector 18 has an analyte-specific binding site for interacting with a fourth specific analyte. The one or more analyte detectors 10 may include any number of analyte detectors having analyte-specific binding sites for interacting with different specific analytes. In an aspect, the analyte-specific binding sites of the analyte detectors are configured to interact with hazardous chemicals.

In an aspect, the analyte-specific binding site causes a change in state of the corresponding analyte detector 10 when a specific analyte interacts with the analyte-specific binding site. In an example, the change in state of the analyte detectors 10 includes a change in an electrical state, such as a change in resistivity or capacitance.

In an aspect, the one or more analyte detectors 10 are configured to permit for increasing a sensitivity for detecting the specific analyte. In an example, the one or more analyte detectors 10 have an input voltage that is adjustable to permit for increased sensitivity of the one or more analyte detectors for the corresponding specific analyte. In another example, the one or more analyte detectors 10 have surface area that is increasable to permit for increased sensitivity of the one or more analyte detectors for the corresponding specific analyte. In another example, the one or more analyte detectors 10 have a reset capability for decreasing a background noise of the one or more analyte detectors 10.

In an example, the analyte detectors include a molecularly imprinted polymer analyte detector. A molecularly imprinted polymer is a polymer that has cavities in polymer matrix with affinity to a chosen molecule. For the molecularly imprinted polymer analyte detector, the molecularly imprinted polymer has a binding site with cavities corresponding to the specific analyte for which the analyte detector is configured to detect. When the specific analyte found in the environment of the analyte detector interacts with a cavity in the polymer matrix, a change in state, such as a change in electrical state, of the analyte detector is caused.

In another example, the analyte detectors include a functionalized carbon nanomaterial analyte detector. The analyte detector includes carbon nanomaterials, such as single walled carbon nanotubes (SWCNT) that are functionalized with receptors that confer selectivity to a chosen analyte. When the specific analyte found in the environment of the analyte detector interacts with the receptors, a change in state, such as a change in electrical state, of the nanomaterials of the analyte detector is caused. In an example, the analyte detectors are derived from flexible hybrid electronic printed systems or integrated flexible sensor substrates that include functionalized carbon nanotube features.

The optical source 20 generates a first frequency comb spectrum 21 directed to an environment to be scanned, the first frequency comb spectrum 21 having multiple optical frequencies at a first frequency range. In an aspect, the optical source 20 further generates a second frequency comb spectrum 22 directed to the environment to be scanned, the second frequency comb spectrum 22 having multiple optical frequencies at a second frequency range. In an example, the first frequency comb spectrum has multiple optical frequencies at a first frequency range of 37-100 THz, and the second frequency comb spectrum has multiple optical frequencies at a second frequency range of 214-400 THz.

In an aspect, the optical source further generates third, fourth, or additional frequency comb spectrums, each of which have multiple optical frequencies at third, fourth, or additional frequency ranges, which may be the same or different from the first and second frequency ranges. By way of example, each frequency range includes a plurality of frequency comb spectrums each having multiple optical frequencies directed into the environment. By way of another example, the different frequency ranges can include ultraviolet, visible, near infrared, mid infrared and long wave infrared regions.

In an aspect, different frequency comb spectrums from different frequency ranges are combined together into a single beam for directing into the environment.

In an aspect, the frequency comb spectrums consist of a series of discrete, equally spaced frequency lines.

At a given time, the multiple optical frequencies of a frequency comb spectrum only cover a portion of the frequency range in which the frequency comb spectrum operates. Scanning of the environment with the frequency comb spectrums includes changing the frequencies of the multiple optical frequencies of the frequency comb spectrum over time to cover the whole frequency range or to cover selected portions of the frequency range.

In an aspect, the optical source 20 directs a frequency comb spectrum into a controlled environment, such as a vapor cell. In an aspect, the one or more analyte detectors 10 are positioned within the same vapor cell. By positioning the one or more analyte detectors 10 within the same controlled environment through which the optical source 20 directs a frequency comb spectrum, the two sensing methods corroborate each other to increase a selectivity of the dual sensor.

In another aspect, the optical source directs one or more frequency comb spectrums into an external environment instead of or in addition to directing a frequency comb spectrum into a controlled environment, such as a vapor cell.

By directing one or more frequency comb spectrums into an environment external to the dual sensor, the dual sensor has ability to operate in a larger geographical area and at a distance to an environment to be scanned.

The frequency comb spectrums of the optical source 20 can be generated by any of a number of systems and methods. An exemplary optical source 20 for generating frequency comb spectrums is represented in the schematic diagram of FIG. 3.

Figure 3:
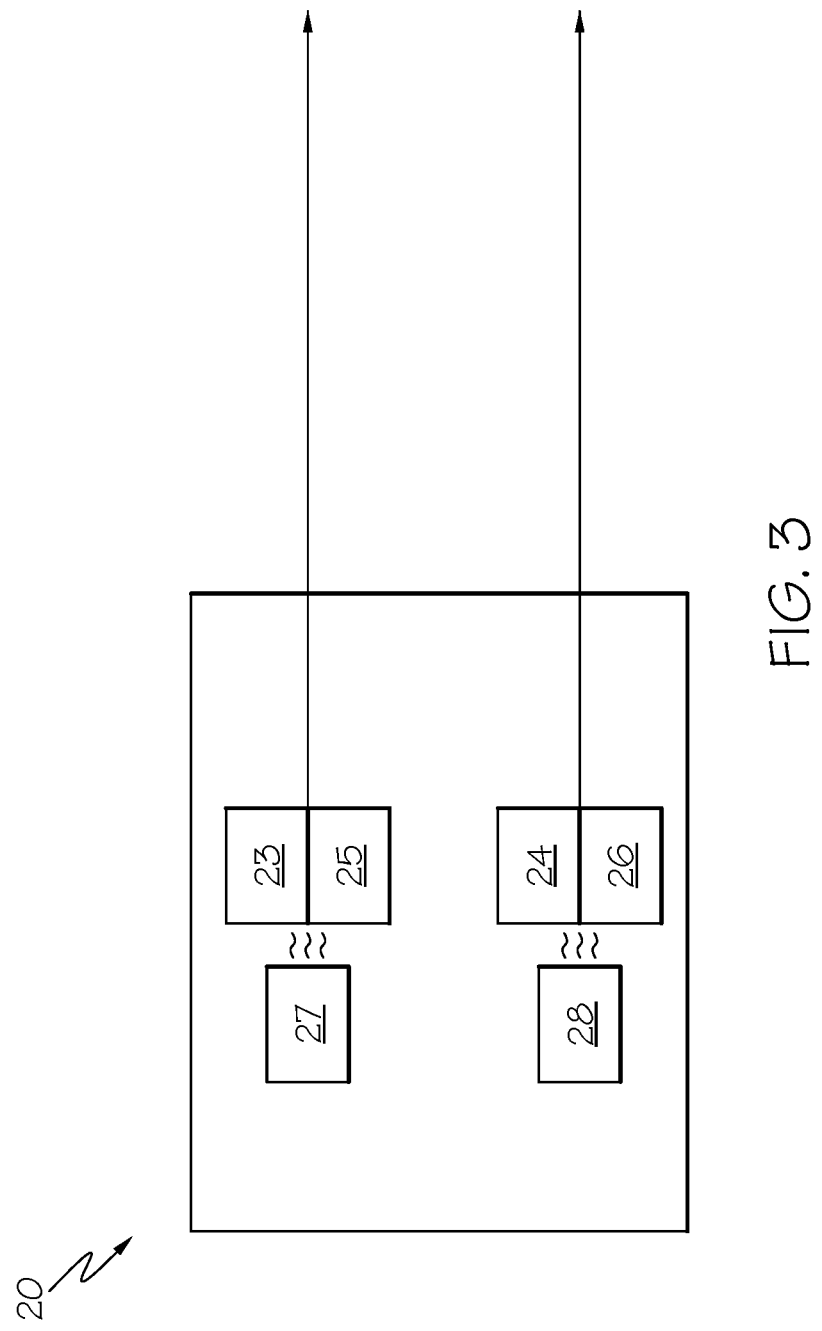
FIG. 3 is a schematic diagram showing an exemplary optical source for generating frequency comb spectrums.

As represented in FIG. 3, the optical source 20 includes a first light source 23, a first micro-resonator 25 coupled to the first light source 23, and a first heater 27 for producing a first frequency comb spectrum 21. In an aspect, the optical source 20 further includes a second light source 24, a second micro-resonator 26 coupled to the second light source 24, and a second heater 28 for producing a second frequency comb spectrum 22. In an aspect, the optical source 20 furthers include third, fourth, and additional light sources, micro-resonators, and heaters for producing third, fourth, and additional frequency comb spectrums.

The first light source 23 provides light at a first frequency range, and the second light source 24 provides light at a second frequency range different from the first frequency range. In an aspect, the light sources include laser light sources.

The first micro-resonator 25 coupled to the first light source 23 generates the first frequency comb spectrum 21 having multiple optical frequencies at the first frequency range, and the second micro-resonator 26 coupled to the second light source 24 generates the second frequency comb spectrum 22 having multiple optical frequencies at the second frequency range.

The first micro-resonator 25 has a resonance adjustable by the first heater 27 for adjusting the frequencies of the multiple optical frequencies of the first frequency comb spectrum 21, and the second micro-resonator 26 has a resonance adjustable by the second heater 28 for adjusting the frequencies of the multiple optical frequencies of the second frequency comb spectrum 22. Thus, the heaters facilitate a scanning of the environment with the frequency comb spectrums by changing the frequencies of the multiple optical frequencies of the frequency comb spectrum over time.

In an example, the optical source 20 include an integrated mid infrared (MIR) optical frequency comb generating a frequency comb spectrum 21 having multiple optical frequencies at a frequency range of 37-100 THz and an integrated near infrared (NIR) optical frequency comb generating a frequency comb spectrum having multiple optical frequencies at a frequency range of 214-400 THz.

The optical source 20 directs the generated frequency comb spectrums to an environment to be scanned. The scanning of the frequency comb spectrums through the environment includes changing the multiple optical frequencies of the respective frequency comb spectrum The optical source 20 is configured to permit for increasing a sensitivity for detecting a specific analyte. In an aspect, optical source 20 is adjusted to scan selected portions of a predetermined spectral range corresponding to an identified specific analyte. In another aspect, the optical source 20 is adjusted is prioritize scanning of selected portions of a predetermined spectral range corresponding to an identified specific analyte. In yet another aspect, the optical source 20 is adjusted is increase a resolution of scanning of selected portions of a predetermined spectral range corresponding to an identified specific analyte.

The use of the optical source generating the first frequency comb spectrum enables for simultaneous detection of tens to hundreds of wavelengths at one time. In addition, the use of the optical source generating more than one frequency comb spectrum provides for covering more than one spectral region enabling for detection of unique features that occur in different spectral regions.

Returning to FIGS. 1 and 2, the optical spectrum analyzer 30 analyzes an optical spectrum resulting from interaction of the first frequency comb spectrum 21 with the environment. In an aspect, the optical spectrum analyzer 30 further analyzes an optical spectrum resulting from interaction of the second frequency comb spectrum 22 with the environment. In an aspect, analysis of an optical spectrum includes receiving an optical spectrum and representing the optical spectrum in the form of data, which can be used to identify presence of chemical in the scanned environment.

According to the arrangement of FIG. 1, the optical spectrum analyzer 30 is arranged to receive fractions of frequency comb spectrum from the optical source 20 after absorption of portions thereof by the environment. In this case, the first frequency comb spectrum 21 and second frequency comb spectrum 22 are transmitted through the environment where a fraction of the first frequency comb spectrum 21 and a fraction of the second frequency comb spectrum 22 are absorbed by the content of the environment. Then, the remaining fractions of the first frequency comb spectrum 21 and second frequency comb spectrum 22 transmitted through the environment are received and analyzed by the optical spectrum analyzer 30.

According to the arrangement of FIG. 2, the optical spectrum analyzer 30 is arranged to receive a backscattered optical spectrum resulting from frequency comb spectrums transmitted from the optical source 20 through the environment. In this case, the first frequency comb spectrum 21 and second frequency comb spectrum 22 are transmitted through the environment where a content of the environment scatters a fraction of the first frequency comb spectrum 21 and a fraction of the second frequency comb spectrum 22. Then, the optical spectrum analyzer 30 receives and analyzes a first backscattered optical spectrum 21' resulting from interaction of the first frequency comb spectrum 21 and a second backscattered optical spectrum 22' resulting from interaction of the second frequency comb spectrum 22 with the environment.

In an example, the optical spectrum analyzer 30 includes a MIR linear detector array configured to detect frequencies in a frequency range of 37-100 THz and a NIR linear detector array configured to detect frequencies in a frequency range of 214-400 THz.

The controller 40 may be any apparatus, system, systems or combinations thereof (e.g., a microprocessor) capable is generating and communicating command signals to achieve a desired result from a controlled device (e.g., the one or more analyte detectors 10, optical source 20, the optical spectrum analyzer 30).

Therefore, in an aspect, the controller 40 is in communication with the one or more analyte detectors 10 to provide commands for adjusting an analyte detector to increase a sensitivity for detecting a specific analyte.

In an aspect, the controller 40 is in communication with the optical source 20 to adjust the first frequency comb spectrum 21 to increase sensitivity for detecting the specific analyte. In another aspect, the controller 40 is in communication with the optical source 20 to adjust the second frequency comb spectrum 22 to increase sensitivity for detecting the specific analyte. By way of example, the controller 40 is in communication with the first heater 27 and/or second heater 28 for adjusting the multiple optical frequencies of the first frequency comb spectrum 21 and/or second frequency comb spectrum 22.

In an aspect, the controller 40 has data correlating the presence of specific analytes in an environment with specific spectral range. Thus, the presence of specific analytes in an environment can have a known spectral signature that is detectable by optical spectroscopy. By way of accessing the data correlating the presence of specific analytes in an environment with specific spectral ranges, the controller can command the optical source 20 to increase sensitivity for detecting the specific analyte by focusing on predetermined spectral ranges.

In an aspect, the controller 40 is configured to identify presence of a specific analyte based on an analyte detector of the one or more analyte detectors 10 and to adjust the first frequency comb spectrum 21 to the predetermined spectral range corresponding to the identified specific analyte. In another aspect, the controller 40 is configured to identify presence of a specific analyte based on an analyte detector of the one or more analyte detectors 10 and to adjust the first frequency comb spectrum 21 and second frequency comb spectrum 22 to predetermined spectral ranges corresponding to the identified specific analyte.

In an aspect, the adjustment to the predetermined spectral ranges includes commanding the optical source 20 to scan selected portions of the predetermined spectral range corresponding to an identified specific analyte, prioritizing the scanning of selected portions of the predetermined spectral range corresponding to an identified specific analyte, and/or increasing a resolution of scanning of selected portions of the predetermined spectral range corresponding to an identified specific analyte.

In another aspect, the controller 40 is configured, where analysis of the optical spectrum resulting from interaction of the first frequency comb spectrum 21 with the environment indicates presence of a specific analyte, to adjust a corresponding analyte detector of the one or more analyte detectors 10 to increase sensitivity for detecting the specific analyte. More specifically, the controller 40 is configured to identify presence of a specific analyte based on the analyzed optical spectrum and to adjust a corresponding analyte detector of the one or more analyte detectors 10 for the identified specific analyte to increase sensitivity for detecting the identified specific analyte.

By way of combining the one or more analyte detectors 10, the optical source 20, the optical spectrum analyzer 30, and the controller 40, the dual sensor enables for providing high sensitivity, improved selectivity, improved reliability, and rapid detection capability in real-time field environments (in contrast to laboratory approaches like mass spectrometry or chemical analysis), which is not present in conventional chemical detection systems.

By the presence of the optical source 20 and optical spectrum analyzer 30, the dual sensor 2 is enabled to identify a chemical by evaluation of the spectra features of the chemical. Moreover, the use the one or more analyte detectors 10 that are highly specific to a single chemical analyte reduces or eliminates a problem of background noise in the optical spectroscopy because the one or more analyte detectors 10 point sensor is not sensitive to the background optical signatures from other chemicals.

Additionally, the analyte detectors can be produced using technology that makes the systems very inexpensive. The size of the systems can be compact, e.g. hundreds of point sensors can be printed on sheet of paper. Also, integrated optical frequency comb systems are available that can be packaged into a format the size of a book.

Moreover, the combination of the one or more analyte detectors 10, the optical source 20, the optical spectrum analyzer 30, and the controller 40 can rapidly accelerate algorithm performance. Together the approaches can provide high sensitivity, high selectivity and high reliability of detection.

In an aspect, the dual sensor is incorporated into military systems, industrial production systems, hazardous chemical systems, and security systems for transpiration of people or packages.

In an aspect, the dual sensor of the present description is incorporated into a mobile sensing system for real-time sensing within in-the-field environments.

In an aspect, the mobile sensing system includes a transmitter for directing the frequency comb spectrums from the optical source 20. In an example, the transmitter includes a beam expander and a beam steering unit for scanning the beam throughout an environment to be scanned.

In an aspect, the mobile sensing system includes a receiver for directing the optical spectrum resulting from interaction of the first frequency comb spectrum 21 with the environment. In an example, the transmitter includes a beam expander in communication with the optical spectrum analyzer 30.

In an aspect, the mobile sensing system includes a global positioning sensor in communication with the controller. By way of the global positioning sensor, the mobile sensing system can document the geographical location of a confirmed detection of a specific analyte.

In an aspect, the mobile sensing system includes a camera in communication with the controller. By way of the camera, the mobile sensing system can document a specific location of a confirmed optical detection of a specific analyte. In an example, the optical source 20 sweeps within an environment external to the mobile sensing systems, and the camera can document the location of where the optical source directs the frequency comb spectrums during a sweep within the environment.

In an aspect, the mobile sensing system includes a network interface and antenna for communicating external to the mobile sensing system. By way of the network interface and antenna, the mobile device can communicate the presence of a positive detection of a specific analyte detected within the scanned environment.

Figure 4:
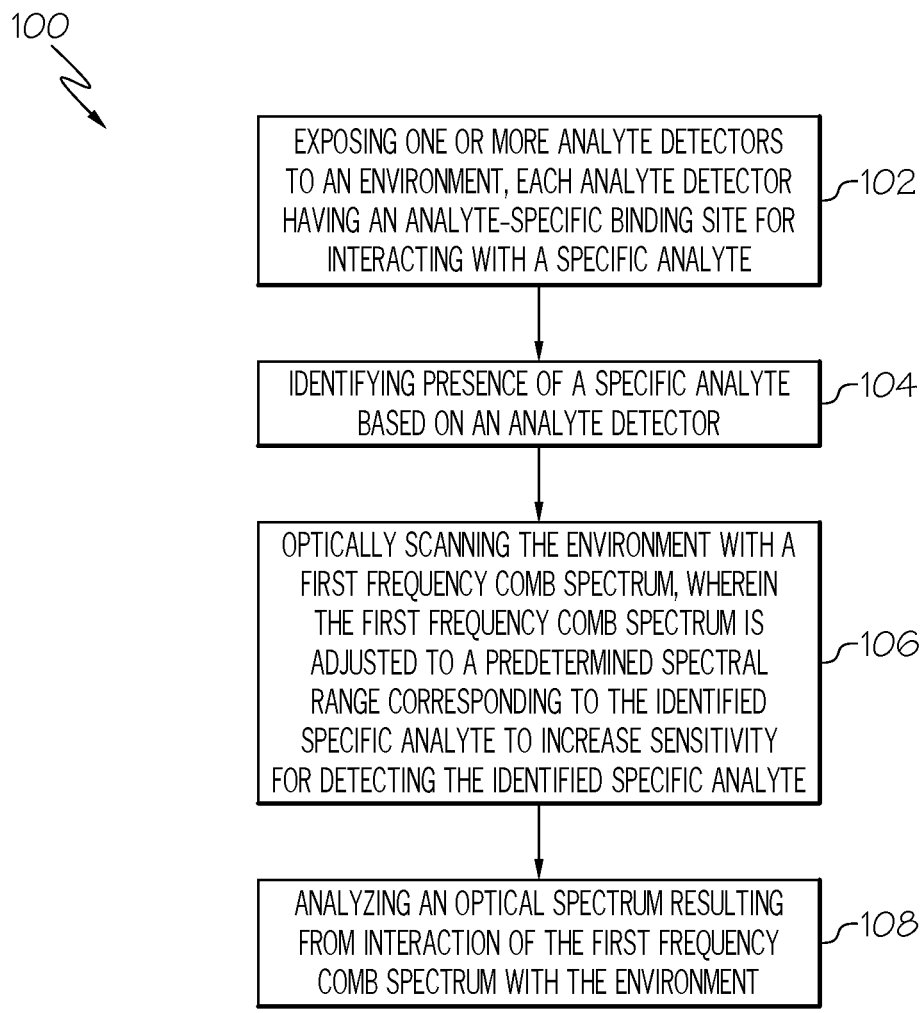
FIG. 4 is a flow diagram of a method for detection of an analyte gas according to the present description.

FIG. 4 is a flow diagram of a method for detection of an analyte gas 100. The method includes: at block 102, exposing one or more analyte detectors to an environment, each analyte detector having an analyte-specific binding site for interacting with a specific analyte; at block 104, identifying presence of a specific analyte based on an analyte detector; at block 106, optically scanning the environment with a first frequency comb spectrum, wherein the first frequency comb spectrum is adjusted to a predetermined spectral range corresponding to the identified specific analyte to increase sensitivity for detecting the identified specific analyte; and at block 108, analyzing an optical spectrum resulting from interaction of the first frequency comb spectrum with the environment.

In an aspect, the step of exposing one or more analyte detectors to the environment includes exposing a plurality of analyte detectors to the environment, each having an analyte-specific binding site for interacting with a different specific analyte.

In another aspect, the method for detection of an analyte gas 100 further includes identifying presence of a specific analyte based on an analyzed optical spectrum and adjusting a corresponding analyte detector for the identified specific analyte to increase sensitivity for detecting the identified specific analyte.

Figure 5:
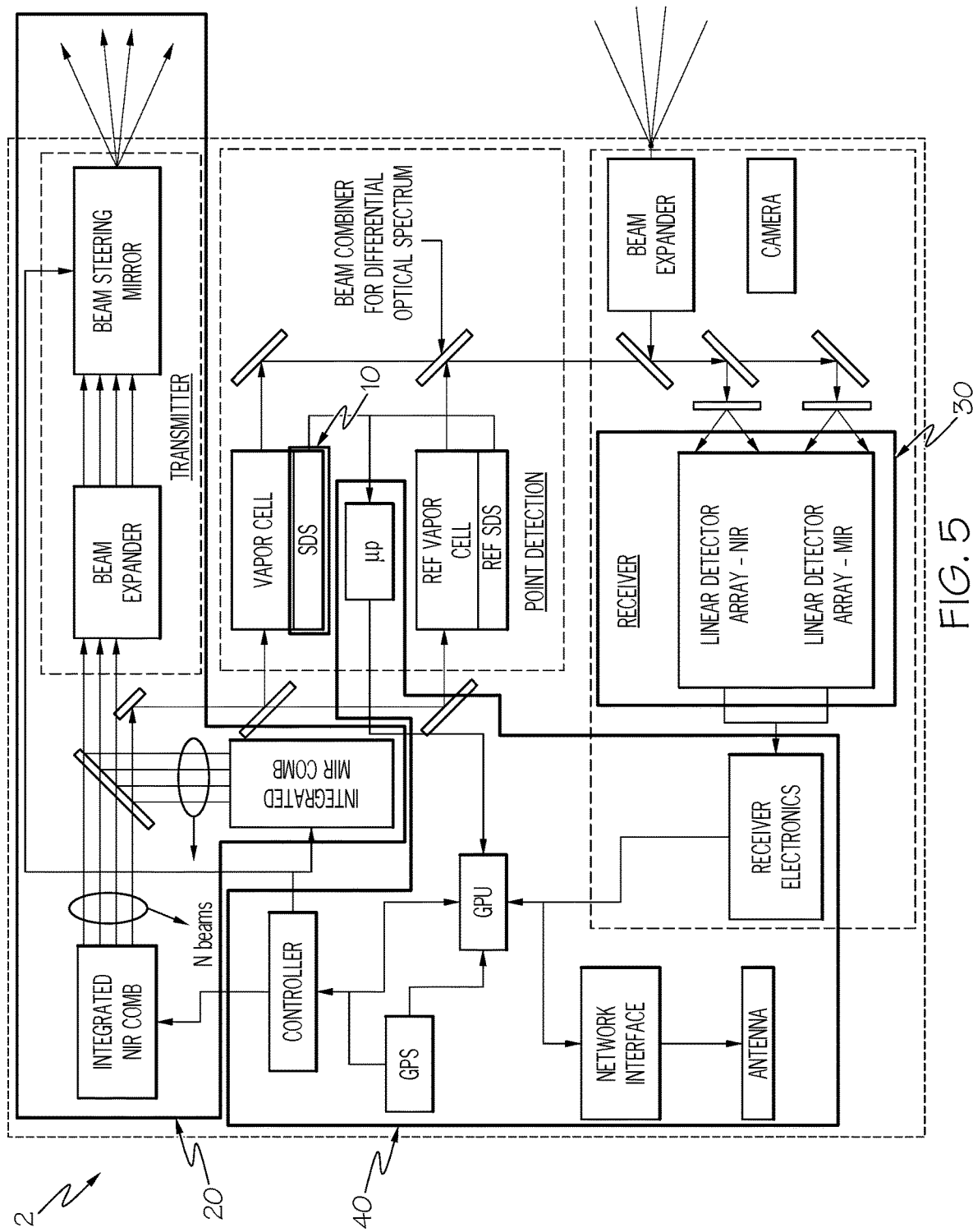
FIG. 5 is an exemplary dual sensor according to the present description.

FIG. 5 is an exemplary dual sensor according to the present description.

As shown in FIG. 5, the dual sensor 2 includes one or more analyte detectors 10, an optical source 20, an optical spectrum analyzer 30, and a controller 40.

As shown, the one or more analyte detectors 10 are positioned in a vapor cell.

As shown, the optical source 20 includes an integrated near-infrared frequency comb and an integrated mid-infrared frequency comb. As represented by the plurality of output lines leaving the integrated near-infrared frequency comb and the integrated mid-infrared frequency comb, the frequency combs produce a plurality of frequency comb spectrums within the respect near-infrared and mid-infrared frequency ranges, and the frequency comb spectrums from the integrated near-infrared frequency comb and the integrated mid-infrared frequency comb are combined into a single beam. The optical source 20 further includes a beam expander and beam steering mirror for directing frequency comb spectrums to an external environment.

As shown, the dual sensor 2 further includes a mirror for directing a frequency comb spectrum to the vapor cell at which the one or more analyte detectors 10 are positioned. As shown, the dual sensor further includes a reference vapor cell having one or more reference analyte detectors and a reference frequency comb spectrum directed to the reference vapor cell.

The dual sensor 2 further includes a beam expander for receiving a backscattered optical spectrum from the external environment and mirrors for directing an optical spectrum exiting the vapor cell and the reference vapor cell.

As shown, the optical spectrum analyzer 30 includes a near-infrared linear detector array and a mid-infrared linear detector array. The near-infrared linear detector analyzes a near-infrared portion of the incoming optical spectrum and the mid-infrared linear detector analyzes a mid-infrared portion of the incoming optical spectrum.

As shown, the controller 40 includes a global positioning sensor (GPS), a general processing unit (GPU), a network interface, an antenna, electronics in communication with the optical spectrum analyzer 30, and a microprocessor associated with the vapor cell.

Thus, the exemplary dual sensor of FIG. 5 detects for the presence of a specific analyte by way of the one or more analyte detectors 10 in the vapor cell after an atmosphere is permitted to enter the vapor cell. The microprocessor associated with the vapor cell monitors the one or more analyte detectors 10. When, the microprocessor indicates presence of a specific analyte, the controller 40 adjusts the frequency comb spectrums of the integrated near-infrared frequency comb and the integrated mid-infrared frequency comb to increase sensitivity for detecting the specific analyte.

The beams from the optical source 20 interrogate the atmosphere within the vapor cell as well as the external environment. The optical spectrum analyzer 30 receives and analyzes the optical spectrum resulting from the interaction of the beams from the optical source 20 with the atmosphere within the vapor cell as well with the external environment.

Where analysis of the optical spectrum resulting from interaction of the frequency comb spectrums indicates presence of a specific analyte, the controller 40 adjusts a corresponding analyte detector of the one or more analyte detectors 10 to increase sensitivity for detecting the specific analyte.

Where analysis of the optical spectrum resulting from interaction of the frequency comb spectrums indicates presence of a specific analyte and the one or more analyte detectors 10 indicates presence of the specific analyte, the controller flags for presence of the specific analyte and the controller can communicate the flag for the presence of the specific analyte via the network interface and antenna.

Figure 6:
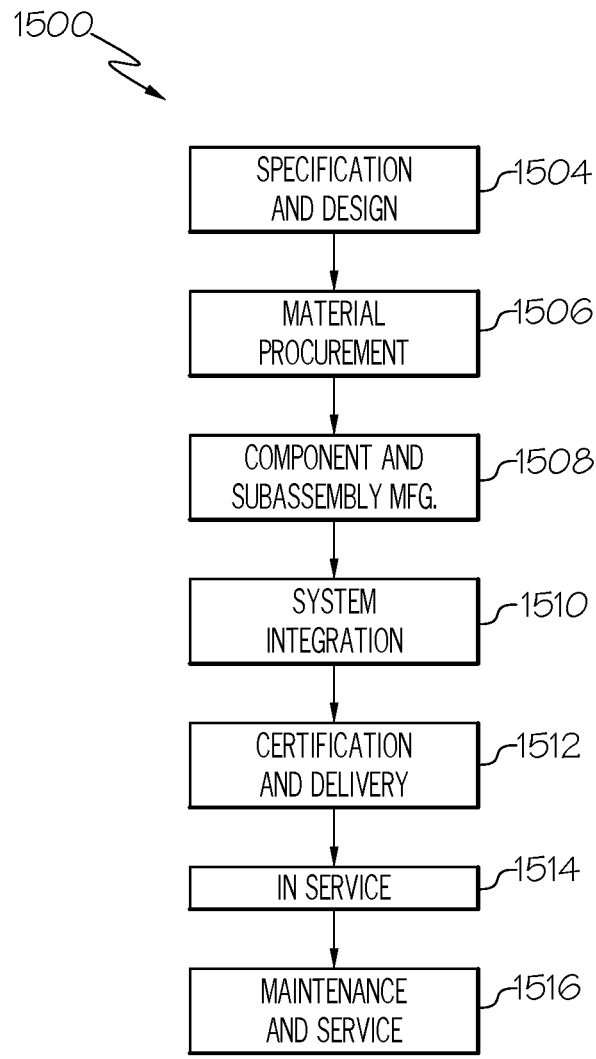
FIG. 6 is flow diagram of an aircraft manufacturing and service methodology.
Figure 7:
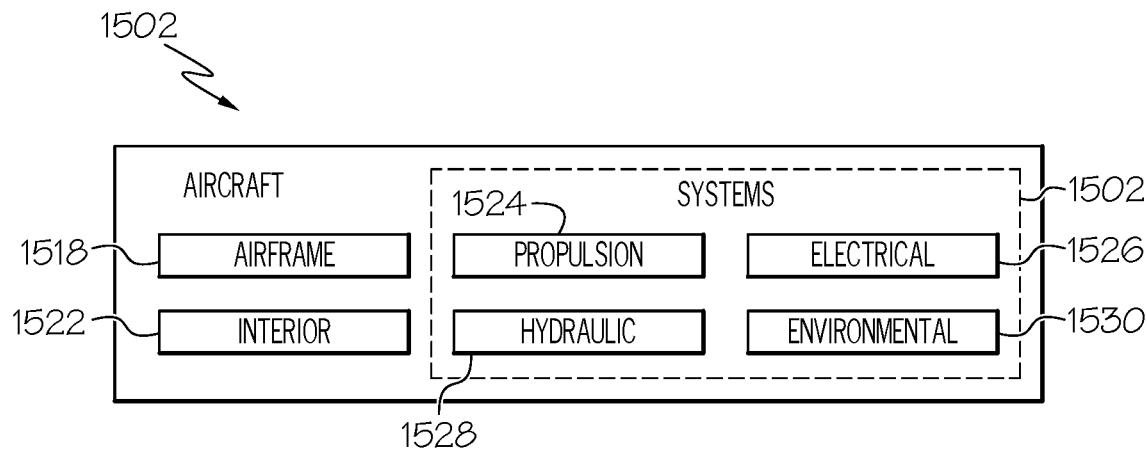
FIG. 7 is a block diagram of an aircraft.

Examples of the present disclosure may be described in the context of an aircraft manufacturing and service method 1500, as shown in FIG. 6, and an aircraft 1502, as shown in FIG. 7. During pre-production, the aircraft manufacturing and service method 1500 may include specification and design 1504 of the aircraft 1502 and material procurement 1506. During production, component/subassembly manufacturing 1508 and system integration 1510 of the aircraft 1502 takes place. Thereafter, the aircraft 1502 may go through certification and delivery 1512 in order to be placed in service 1514. While in service by a customer, the aircraft 1502 is scheduled for routine maintenance and service 1516, which may also include modification, reconfiguration, refurbishment and the like.

Each of the processes of method 1500 may be performed or carried out by a system integrator, a third party, and/or an operator (e.g., a customer). For the purposes of this description, a system integrator may include without limitation any number of aircraft manufacturers and major-system subcontractors; a third party may include without limitation any number of venders, subcontractors, and suppliers; and an operator may be an airline, leasing company, military entity, service organization, and so on.

The methods and systems for forming perforated composite structures of the present disclosure may be employed during any one or more of the stages of the aircraft manufacturing and service method 1500, including specification and design 1504 of the aircraft 1502, material procurement 1506, component/subassembly manufacturing 1508, system integration 1510, certification and delivery 1512, placing the aircraft in service 1514, and routine maintenance and service 1516.

As shown in FIG. 7, the aircraft 1502 produced by example method 1500 may include an airframe 1518 with a plurality of systems 1520 and an interior 1522. Examples of the plurality of systems 1520 may include one or more of a propulsion system 1524, an electrical system 1526, a hydraulic system 1528, and an environmental system 1530. Any number of other systems may be included. The methods and systems for forming perforated composite structures of the present disclosure may be employed for any of the systems of the aircraft 1502.

Although various embodiments of the disclosed dual sensor and method for detection of an analyte gas have been shown and described, modifications may occur to those skilled in the art upon reading the specification. The present application includes such modifications and is limited only by the scope of the claims.

What is claimed is:

1. A dual sensor comprising:
one or more analyte detectors, each having an analyte-specific binding site for interacting with a specific analyte;
an optical source configured to generate a first frequency comb spectrum directed to an environment to be scanned, wherein the first frequency comb spectrum has multiple optical frequencies at a first frequency range;
an optical spectrum analyzer configured to analyze an optical spectrum resulting from interaction of the first frequency comb spectrum with the environment, wherein the analyzed optical spectrum includes a back-scattered optical spectrum resulting from interaction of the first frequency comb spectrum with the environment; and
a controller configured, where an analyte detector indicates presence of a specific analyte, to adjust the first frequency comb spectrum to increase sensitivity for detecting the specific analyte.

2. The dual sensor of claim 1 wherein the optical source comprises a first light source providing light at the first frequency range.

3. The dual sensor of claim 2 wherein the optical source further comprises a first micro-resonator coupled to the first light source, wherein the first frequency comb spectrum is generated by a first micro-resonator coupled to the first light source.

4. The dual sensor of claim 3 wherein the optical source further comprises a first heater, wherein the first micro-resonator has a resonance adjustable by the first heater for adjusting the multiple optical frequencies of the first frequency comb spectrum.

5. The dual sensor of claim 1 wherein the controller is configured to identify presence of an analyte based on an analyte detector and to adjust the first frequency comb spectrum to a predetermined spectral range corresponding to the identified analyte.

6. The dual sensor of claim 1 wherein the controller is configured, where analysis of the optical spectrum resulting from interaction of the first frequency comb spectrum with the environment indicates presence of an analyte, to adjust a corresponding analyte detector to increase sensitivity for detecting the analyte.

7. The dual sensor of claim 6 wherein the controller is configured to identify presence of an analyte based on the analyzed optical spectrum and to adjust a corresponding analyte detector for the identified analyte to increase sensitivity for detecting the identified analyte.

8. The dual sensor of claim 1 wherein the analyzed optical spectrum includes a fraction of the first frequency comb spectrum transmitted through the environment.

9. The dual sensor of claim 1 wherein the one or more analyte detectors is a plurality of analyte detectors, each having an analyte-specific binding site for interacting with a different specific analyte.

10. The dual sensor of claim 1 wherein the one or more analyte detectors include at least one of a molecularly imprinted polymer and a functionalized carbon nanotube.

11. A dual sensor, comprising:
a plurality of analyte detectors, each having an analyte-specific binding site for interacting with a different specific analyte;
an optical source configured to generate a first frequency comb spectrum and a second frequency comb spectrum directed to the environment to be scanned, wherein the first frequency comb spectrum has multiple optical frequencies at a first frequency range and the second frequency comb spectrum having multiple optical frequencies at a second frequency range different from the first frequency range;
an optical spectrum analyzer configured to analyze an optical spectrum resulting from interaction of the first and second frequency comb spectrums with the environment, wherein the optical spectrum analyzer is configured to receive backscattered optical spectrum resulting from interaction of the first frequency comb spectrum with the environment; and
a controller configured, where an analyte detector indicates presence of a specific analyte, to adjust the first and second frequency comb spectrums to increase sensitivity for detecting the specific analyte.

12. The dual sensor of claim 11 wherein the optical source comprises a first light source providing light at the first frequency range for the first frequency comb spectrum and a second light source providing light at the second frequency range for the second frequency comb spectrum.

13. The dual sensor of claim 12 wherein the optical source further comprises a first micro-resonator coupled to the first light source and a second micro-resonator coupled to the second light source, wherein the first frequency comb spectrum is generated by a first micro-resonator coupled to the first light source and the second frequency comb spectrum is generated by a second micro-resonator coupled to the second light source.

14. The dual sensor of claim 13 wherein the optical source further comprises a first heater and a second heater, wherein the first micro-resonator has a resonance adjustable by the first heater for adjusting the multiple optical frequencies of the first frequency comb spectrum, and wherein the second micro-resonator has a resonance adjustable by the second heater for adjusting the multiple optical frequencies of the second frequency comb spectrum.

15. The dual sensor of claim 11 wherein the plurality of analyte detectors include at least one of a molecularly imprinted polymer and a functionalized carbon nanotube.

16. The dual sensor of claim 11 wherein the first frequency comb spectrum has the multiple optical frequencies at a frequency range of 37-100 THz, and wherein the second frequency comb spectrum has the multiple optical frequencies at a frequency range of 214-400 THz.

17. A method for detection of an analyte gas, the method comprising:
exposing one or more analyte detectors to an environment, each analyte detector having an analyte-specific binding site for interacting with a specific analyte;
identifying presence of a specific analyte based on an analyte detector;
optically scanning the environment with a first frequency comb spectrum, wherein the first frequency comb spectrum is adjusted to a predetermined spectral range corresponding to the identified specific analyte to increase sensitivity for detecting the identified specific analyte; and
analyzing an optical spectrum resulting from interaction of the first frequency comb spectrum with the environment, wherein the analyzed optical spectrum includes a backscattered optical spectrum resulting from interaction of the first frequency comb spectrum with the environment.

18. The method of claim 17 wherein the step of exposing one or more analyte detectors to the environment includes exposing a plurality of analyte detectors to the environment, each having an analyte-specific binding site for interacting with a different specific analyte.

19. The method of claim 17 further comprising identifying presence of an analyte based on an analyzed optical spectrum and adjusting a corresponding analyte detector for the identified analyte to increase sensitivity for detecting the identified analyte.

20. A dual sensor comprising:
one or more analyte detectors, each having an analyte-specific binding site for interacting with a specific analyte;
an optical source configured to generate a first frequency comb spectrum directed to an environment to be scanned, wherein the first frequency comb spectrum has multiple optical frequencies at a first frequency range, wherein the optical source comprises:
a first light source configured to provide light at the first frequency range;
a first micro-resonator coupled to the first light source, wherein the first frequency comb spectrum is configured to be generated by the first micro-resonator; and
a first heater, wherein the first micro-resonator has a resonance adjustable by the first heater for adjusting the multiple optical frequencies of the first frequency comb spectrum;
an optical spectrum analyzer configured to analyze an optical spectrum resulting from interaction of the first frequency comb spectrum with the environment; and
a controller configured, where an analyte detector indicates presence of a specific analyte, to adjust the first frequency comb spectrum to increase sensitivity for detecting the specific analyte.

* * * * *